United States Patent [19]
Humphrey et al.

[11] Patent Number: 5,696,266
[45] Date of Patent: *Dec. 9, 1997

[54] PROCESS FOR THE STEREOSELECTIVE REDUCTION OF STEROID ENELACTAMS

[75] Inventors: Guy R. Humphrey, Belle Mead; Ross A. Miller, Fanwood, both of N.J.

[73] Assignee: Merck & Co., Inc., Rahway, N.J.

[*] Notice: The term of this patent shall not extend beyond the expiration date of Pat. No. 5,470,976.

[21] Appl. No.: 508,804

[22] Filed: Jul. 28, 1995

Related U.S. Application Data

[63] Continuation-in-part of Ser. No. 301,949, Sep. 7, 1994, Pat. No. 5,470,976.

[51] Int. Cl.$^6$ ............................................. C07D 221/18
[52] U.S. Cl. ........................................ 546/77; 546/78
[58] Field of Search ............................ 546/77, 78; 514/284

[56] References Cited

U.S. PATENT DOCUMENTS

| | | | |
|---|---|---|---|
| 4,220,775 | 9/1980 | Rasmusson et al. | 546/77 |
| 4,377,584 | 3/1983 | Rasmusson et al. | 546/77 |
| 4,760,071 | 7/1988 | Rasmusson et al. | 546/77 |
| 4,845,104 | 7/1989 | Carlin et al. | 546/77 |
| 5,049,562 | 9/1991 | Rasmusson et al. | 546/77 |
| 5,061,801 | 10/1991 | Williams et al. | 546/77 |
| 5,061,802 | 10/1991 | Steinberg et al. | 546/77 |
| 5,061,803 | 10/1991 | Williams | 546/77 |
| 5,075,450 | 12/1991 | Rasmusson et al. | 546/77 |
| 5,091,380 | 2/1992 | Rasmusson et al. | 552/610 |
| 5,091,534 | 2/1992 | King et al. | 546/77 |
| 5,098,908 | 3/1992 | Steinberg et al. | 546/77 |
| 5,120,742 | 6/1992 | Rasmusson et al. | 546/77 |
| 5,138,063 | 8/1992 | Rasmusson et al. | 546/77 |
| 5,151,429 | 9/1992 | Rasmusson et al. | 546/77 |
| 5,151,430 | 9/1992 | Steinberg et al. | 546/77 |
| 5,162,332 | 11/1992 | Taylor et al. | 514/252 |
| 5,196,411 | 3/1993 | Rasmusson et al. | 514/169 |
| 5,215,894 | 6/1993 | Arison et al. | 546/77 |
| 5,237,061 | 8/1993 | Bhattacharya et al. | 546/77 |
| 5,237,064 | 8/1993 | Bakshi et al. | 546/77 |
| 5,237,067 | 8/1993 | Schumaker | 546/187 |
| 5,278,159 | 1/1994 | Bakashi et al. | 546/77 |
| 5,304,562 | 4/1994 | Biollaz | 514/284 |
| 5,324,734 | 6/1994 | Gilbert et al. | 546/77 |
| 5,470,976 | 11/1995 | Humphrey et al. | 546/77 |
| 5,525,608 | 6/1996 | Adams et al. | 546/77 |
| 5,536,727 | 7/1996 | Witzel et al. | 546/77 |

FOREIGN PATENT DOCUMENTS

| | | |
|---|---|---|
| 1465544 | 11/1965 | France. |
| 3612632 | 10/1987 | Germany. |
| WO 93/23038 | 11/1993 | WIPO. |
| WO 93/23039 | 11/1993 | WIPO. |
| WO 93/23040 | 11/1993 | WIPO. |
| WO 93/23041 | 11/1993 | WIPO. |
| WO 93/23048 | 11/1993 | WIPO. |
| WO 93/23050 | 11/1993 | WIPO. |
| WO 93/23051 | 11/1993 | WIPO. |
| WO 93/23419 | 11/1993 | WIPO. |
| WO 93/23420 | 11/1993 | WIPO. |
| WO 94/07861 | 4/1994 | WIPO. |
| WO 95/00147 | 1/1995 | WIPO. |
| WO 95/11254 | 4/1995 | WIPO. |
| WO 95/12398 | 5/1995 | WIPO. |

OTHER PUBLICATIONS

Lepor, H. Proc. of Am. Urological A'ssn, vol. 155 May 1996 Supplement p. 587A, abstract 1105.

Sakurai et al., Tetrahedron, vol. 46, No. 3 (1990), pp. 761–774, "Stereocontrolled synthesis of (–)-prezizanol, (–)-prezizaene, their epimers and (–)-allokhusiol".

Templeton et al., J. Chem. Soc. Perk., vol. 1, No. 6 (1987), pp. 1361–1368, "Synthesis of ring–A and –B substituted 17alpha–acetoxypregnan–20–one derivatives . . .".

Larpent et al., Tetra. Letters, vol. 28, No. 22 (1987), pp. 2507–2510, "Catalytic hydrogenation of olefins in biphasic water–liquid system".

Kharchenko et al., Zh. Org. Khim., vol. 23, No. 3 (1987), pp. 576–581, "Stereoselective synthesis of hydroxanthenes".

Abad et al., Tetra. Letters, vol. 27, No. 28 (1986), pp. 3289–3292, "An approach to erythrophleum alkaloids. Synthesis of methyl(–)-4–epi–cassamate".

Stork et al., J. Am. Chem. Soc., vol. 105 (1983), pp. 1072–1073, "Stereocontrol in homogeneous catalytic hydrogenation via hydroxyl group coordination".

Suggs et al., Tetra. Letters, vol. 72 (1981), pp. 303–306, "Facile homogeneous hydrogenations of hindered olefins with [1r(cod)py(PCy3)PF6]".

Kollar et al., J. Molecular Catalysis, vol. 47, No. 3 (1988), pp. 33–39, "Stereoselective reduction of steroids with in situ prepared phosphine rhodium catalysts".

Harris et al., Proc. Natl. Acad. Sci. USA, vol. 89 (1992), pp. 10787–10791, "Identification and selective inhibition of an isozyme of steroid 5alpha–reductase in human scalp".

Doyle et al., J. Org. Chem., vol. 43, No. 4 (1978), pp. 693–696, "Silane reductions in acidic media, 10. ionic hydrogenation of cycloalkenes, stereoselectivity and mechanism".

Rasmusson et al., J. Med. Chem., vol. 27 (1984), pp. 1690–1701, "Azasteroids as inhibitors of rat prostatic 5alpha–reductase".

Rasmusson et al., J. Med. Chem., vol. 29 (1986), pp. 2298–2315, "Azasteroids: Structure–activity relationships for inhibtion of 5alpha–reductase and of androgen receptor binding".

(List continued on next page.)

*Primary Examiner*—Donald G. Daus
*Attorney, Agent, or Firm*—Catherine D. Fitch; Melvin Winokur

[57] ABSTRACT

The novel process of this invention involves the reduction of certain Δ-5 steroidal alkenes to selectively produce either the 5α or 5β reduction products. Particularly, this invention involves reduction of Δ-5 steroidal alkenes using a rhodium based catalyst in the presence of hydrogen to selectively yield 5α steroids or alternatively reduction of Δ-5 steroidal alkenes in an ionizing medium with a trialkylsilane to selectively yield 5β steroids.

15 Claims, No Drawings

OTHER PUBLICATIONS

Jones et al., J. Med. Chem., vol. 36 (1993), pp. 421–423, "Nonsteroidal inhibitors of human type I steroid 5–alpha–reductase".

Cannon et al., Synthesis Commun. (Jun. 1986), pp. 494–496, "Stereospecific route to trans–1,2,3,4,4a,5,6,10b–octahydrobenzo[f]quinolines".

Murahashi et al., J. Org. Chem., vol. 57 (1992), pp. 2521–2523, "Ruthenium–catalyzed hydration of nitriles and transformation of –keto nitriles to ene–lactams".

Boyle et al., Urology, "Prostate Volume Predicts Outcome of Treatment of Benign Prostatic Hyperplasia with Finasteride: Meta–Analysis of Randomized Clinical Trials", vol. 48, No. 3, Sep. 1996, pp. 398–405.

PROCESS FOR THE STEREOSELECTIVE REDUCTION OF STEROID ENELACTAMS

CROSS REFERENCE TO RELATED APPLICATIONS

This application is a continuation-in-part of U.S. Ser. No. 08/301,949, filed Sep. 7, 1994 U.S. Pat. No. 5,470,976.

FIELD OF THE INVENTION

The present invention is concerned with a novel process for the stereoselective reduction of enelactams. The process is particularly useful for the reduction of Δ-5 steroidal enelactams.

BACKGROUND OF THE INVENTION

The principal mediator of androgenic activity in some target organs, e.g., the prostate, is 5α-dihydrotestosterone ("DHT"), formed locally in the target organ by the action of 5α-reductase, which converts testosterone to DHT. Certain undesirable physiological manifestations, such as acne vulgaris, seborrhea, female hirsutism, androgenic alopecia (also called androgenetic alopecia) which includes female and male pattern baldness, and benign prostatic hyperplasia, are the result of hyperandrogenic stimulation caused by an excessive accumulation of testosterone ("T") or similar androgenic hormones in the metabolic system. Inhibitors of 5α-reductase will serve to prevent or lessen symptoms of hyperandrogenic stimulation in these organs. See especially U.S. Pat. No. 4,377,584, issued Mar. 22, 1983, and U.S. Pat. No. 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., Proc. Natl. Acad. Sci. USA, Vol. 89, pp. 10787–10791 (Nov. 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

The reduction of Δ-5 steroidal alkenes to the corresponding saturated compounds is an important step in the synthesis of steroid end-products useful as 5α-reductase inhibitors.

Platinum, palladium/carbon, and noble metals such as nickel have been previously used as catalysts in the reduction of Δ-5 steroidal enelactams to preferentially yield the corresponding 5α-steroid. The degree of selectivity varies according to the particular steroidal enelactam being reduced. The best selectivity achieved using these catalysts to reduce 4,7β-dimethyl-4-aza-cholest-5-ene-3-one and its 4-NH analog is about 100:1 of α:β product. Because the resulting α/β mixture can be purified only with great difficulty, it was desirable to develop a reduction process exhibiting greater selectivity for the α-reduction product. Furthermore, none of the previously described reductions, catalytic or otherwise, offered any way to selectively direct hydrogenation to obtain the 5β reduction products which are also useful as 5α-reductase inhibitors.

The instant invention provides an improved method for stereoselective reduction of certain Δ-5 steroidal enelactams. In the case of 4,7β-dimethyl-4aza-cholest-5-ene-3-one, process parameters can be adjusted to preferentially yield the α-reduction product over the β-reduction product in a ratio of about 500:1. The α-reduction product of 7β-methyl-4 aza-cholest-5-ene-3-one is selectively formed over the β-reduction product in a ratio of about 264:1. Alternatively, the process parameters can be varied to selectively yield the β-reduction product of 4,7β-dimethyl-4 aza-cholest-5-ene-3-one and its 4-NH analog over the α-reduction products by ratios of about 60:1 and 90:1 respectively.

SUMMARY OF THE INVENTION

The novel process of this invention involves the reduction of certain Δ-5 steroidal alkenes to selectively produce either the 5α or 5β reduction products. Particularly, this invention involves reduction of Δ-5 steroidal alkenes using a rhodium based catalyst in the presence of hydrogen to selectively yield 5α steroids or alternatively reduction of Δ-5 steroidal alkenes in an ionizing medium with a trialkylsilane to selectively yield 5β steroids. This novel process can be exemplified in the following embodiment.

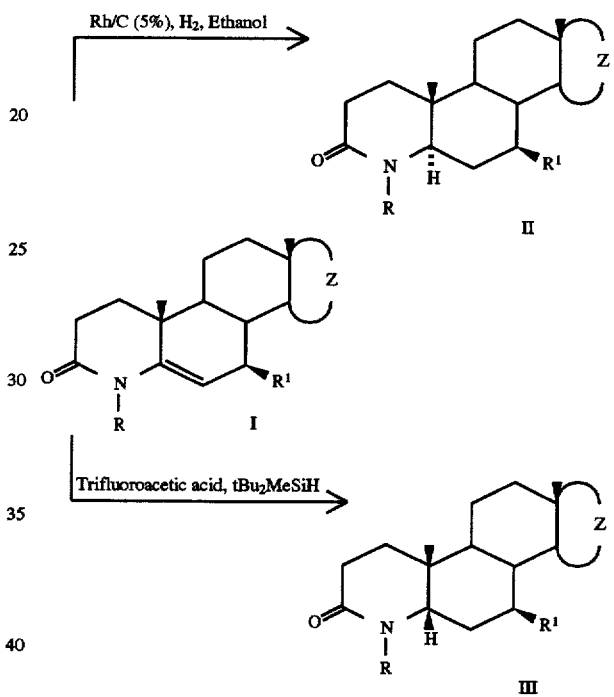

wherein R is selected from H and $C_1$–$C_5$ alkyl, $R^1$ is selected from $C_{1-5}$ alkyl and phenyl, and Z is

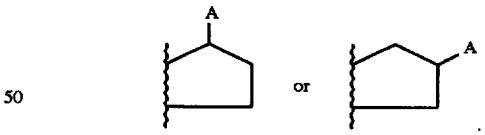

The α-reduction product corresponding to Formula II and the β-reduction product corresponding to Formula III are useful as 5α-reductase inhibitors or as intermediates in the preparation of 5α-reductase inhibitors. 5α-reductase inhibitors are useful in the treatment of hyperandrogenic disorders such as benign prostatic hyperplasia, acne vulgaris, seborrhea, female hirsutism, androgenic alopecia (androgenetic alopecia), including male pattern baldness, and the prevention and treatment of prostatic carcinoma.

DETAILED DESCRIPTION OF THE INVENTION

The novel process of this invention allows for greater stereoselective control than previously possible over the reduction of Δ-5 steroid enelactams.

Reduction of Δ-5 steroidal enelactams to 5α-steroidal lactams using platinum, palladium/carbon, and noble metals such as nickel catalysts is described in U.S. Pat. No. 5,237, 064, issued Aug. 17, 1993. The degree of selectivity varies according to the particular steroidal enelactam being reduced. The best selectivity achieved using these catalysts to reduce 4,7β-dimethyl-4 aza-cholest-5-ene-3-one and its 4-NH analog is about 100:1 of α:β product. Because the resulting α/β mixture can be purified only with great difficulty, it was desirable to develop a reduction process exhibiting greater selectivity for the α-reduction product. The process of the present invention leads to stereoselective α/β ratio at least twice that of the prior reductions.

Acidic hydride reductions of various fused ring alkenes have been reported in which one stereoisomer product predominates depending on the nature of the alkene substrate. Bulky silanes have been used to provide high selectivity in the reduction of a non heteroatom stabilized alkene (octahydronaphthalene to decahydro-naphthalene), with the β product predominating. See Doyle, M. P., McOsker, C. C., *J. Org. Chem.*, 43(4), 693–696 (1978). Acidic hydride reduction of ene-lactams, however, has been reported to reduce ene-lactam with the 5α- product predominating. See, e.g., Rasmusson, et al., *J. Med. Chem.*, 27, 1690 (1984); Rasmusson, et al., *J. Med. Chem.*, 29, 2298 (1986); Jones, et al., *J. Med. Chem.*, 36, 421 (1993); Cannon, et al., *Synthesis*, 494 (1986); and Murahashi, et al., *J. Org. Chem.*, 2521 (1992). The process of the present invention offers a way to selectively obtain the 5β-reduction products of Δ-5 steroid enelactams by exploiting the surprising discovery that, contrary to published reports, ionic reductions of enelactams favor β face selectivity.

In one embodiment of this invention, a Δ-5 steroidal enelactam is dissolved in solvent and treated with $H_2$ in the presence of a rhodium-based catalyst selected from $Rh/Al_2O_3$ (5%) or Rh/C (5%) to preferentially obtain the α-reduction product.

In exemplifications of this invention where Rh/C (5%) is employed as the catalyst, the solvent used is a $C_{1-6}$ alcohol, such as methanol, ethanol, n-propanol, isopropanol, etc. In particular, the preferred solvent in the Rh/C catalyzed system is ethanol. When using $Rh/Al_2O_3$ (5%) as the catalyst, the solvent is a $C_{1-4}$ alkanoic acid, such as formic, acetic, propionic, or butyric acid. In particular, the preferred solvent in the $Rh/Al_2O_3$ catalyzed system is acetic acid.

Those skilled in the art are familiar with the use of catalytic amounts of reaction catalysts and will appreciate that the amount of catalyst that can be used may vary with the scale of the reaction. Generally, the amount of rhodium based catalyst used in the process of the present invention is adjusted so that the weight of rhodium present in the reaction mixture represents between 5–100% and preferably between 10–20% of the weight of the Δ-5 steroid alkene starting material. In particular, a weight of rhodium corresponding to about 20% of the Δ-5 steroid alkene starting material weight is preferred.

The catalytic reduction is preferably run at a $H_2$ pressure of 40 psi, but pressure may be increased to as much as 250 psi in order to reduce the reaction time.

The rhodium catalyzed reduction can be optimally run between about 20°–30° C. and may be conveniently run at room temperatures within this range. Temperatures above this range will adversely affect the selectivity of reduction and it is most preferable to maintain the reaction at the lower temperatures within this range.

A second embodiment of the present invention involves refluxing a Δ-5 steroidal enelactam in an ionizing medium such as trifluoroacetic acid with a trialkylsilane to preferentially yield the 5β-azasteroid product. Trialkylsilanes usable in the process of the present invention have the formula $(R^2)_3SiH$ in which each alkyl group represented by $R^2$ may be independently selected from $C_{1-6}$ alkyl and phenyl. In particular, trifluoroacetic acid is the preferred ionizing medium with di-t-butylmethylsilane and tri-t-butylsilane being the preferred trialkylsilanes usable in this embodiment of the invention.

The process of the present invention is useful for the stereoselective reduction of Δ-5 steroidal enelactams. The process is particularly useful for the steroidal reduction of Δ-5 steroidal enelactams of formula I:

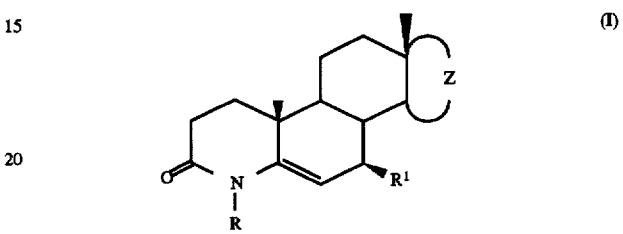

(I)

wherein:

R is selected from H and $C_1$–$C_5$ alkyl;

$R^1$ is selected from $C_{1-5}$ alkyl and phenyl, and Z is selected from

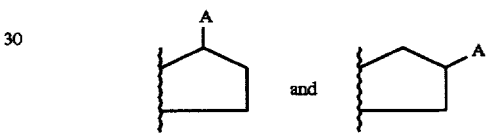

The oxidation reaction is not affected by the substituent at the 16- or 17-position of the steroid, and thus "A" can be any synthetically feasible substituent. The flexibility and broad applicability of the instant process is demonstrated by the fact that it is not limited by the choice of substituent at the 16- and 17-positions of the steroidal starting material.

Representative examples of "A" include but are not limited to: —H; keto (=O); protected hydroxy, e.g. dimethyl-t-butyl silyloxy, trimethylsilyloxy, triethylsilyloxy, tri-isopropylsilyloxy, triphenylsilyloxy; acetate; hydroxy; carboxy, protected amino, e.g. acetylamino; amino; $C_{1-10}$ alkyl, e.g. methyl, ethyl, propyl, butyl, pentyl, 1,5-dimethylhexyl, 6-methylhept-2-yl cholestanyl 17-side chain, pregnane or stigmasterol 17-side chain; substituted or unsubstututed $C_{1-10}$ alkenyl, e.g. phenylmethylene, chlorophenylmethylene, ethoxycarbonylphenylmethylene, carboxyphenylmethylene, (((1,1-dimethylethyl)amino)carbonyl)phenylmethylene, trimethoxyphenyl methylene, methoxyphenylmethylene, methylsulfonylphenylmethylene, biphenylmethylene, nitrophenylmethylene, aminophenylmethylene, acetylaminophenylmethylene, pivaloylaminophenylmethylene, phenoxyphenylmethylene, 2-imidazolyl methylene, 2-thiazolylmethylene; aryl substituted $C_{1-10}$ alkyl, e.g. omegaphenylpropyl, 1-(chlorophenoxy)ethyl; aryl, e.g. phenyl, pyridinyl and pyrimidinyl; substituted aryl, e.g. phenyl, pyridinyl and pyrimidinyl substituted with one to three substituents independently selected from:

(1) —H, (2) —OH, (3) —$CH_3$, (4) —OCH$_3$, (5) —S(O)$_n$—CH$_3$, wherein n is selected from 0, 1, and 2, (6) —CF$_3$, (7) halo, (8) —CHO, (9) CN, and

(10) —NHR$^7$, wherein R$^7$ is selected from:
—H, —C$_{1-8}$ alkyl, —C$_{1-6}$ alkylcarbonyl, —C$_{1-6}$ alkylsulfonyl, and —C$_{1-6}$ alkoxycarbonyl, aryl carbamoyl substituted C$_{1-10}$ alkyl, e.g. 2-(4-pyridinyl-carbamoyl)ethyl; C$_{1-10}$alkylcarbonyl, e.g. isobutylcarbonyl; arylcarbonyl, e.g. phenylcarbonyl; ether-substituted C$_{1-10}$alkyl, e.g. 1-methoxy-ethyl, 1-ethoxy-ethyl; keto-substituted C$_{1-10}$alkyl, e.g. 1-ketoethyl, ketomethyl, 1-ketopropyl, and ketobutyl; heteroaryl-substituted C$_{1-10}$ alkyl, e.g. omega-(4-pyridyl)-butyl; carboxylic esters, e.g. C$_{1-10}$ alkylcarboxylic esters such as carbomethoxy and carboethoxy; carboxamides, e.g. C$_{1-10}$ alkylcarboxamides or aralkylcarboxamides such as N,N-diisopropyl carboxamide, N-t-butyl carboxamide, N-(hydroxyphenyl)carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetylcarboxamide, N-acetamidophenyl-carboxamide, N-pivalamidophenyl carboxamide, N-isobutyramidophenyl carboxamide, N-(methyl),N-(diphenylmethyl)carboxamide, and N-(diphenylmethyl)-carboxamide; carbamates such as C$_{1-10}$ alkylcarbamates, especially t-butylcarbamate and isopropyl carbamate; substituted or unsubstituted anilide derivatives, e.g. N-substituted-phenyl-carboxamides wherein the phenyl may be substituted with 1 to 2 substituents selected from ethyl, methyl, trifluoromethyl or halo (F, Cl, Br, I); C$_{1-10}$alkanoyloxy C$_{1-2}$alkyl, e.g. acetyloxymethyl, trimethylacetyloxy methyl, and (2-ethylhexanoyloxy)methyl; ureas, e.g. C$_{1-10}$ alkylcarbonylamino ureas such as t-butylcarbonylamino urea; C$_{1-10}$ alkylureido C$_{0-5}$ alkyl, e.g., N-t-butylureidomethyl, N-n-propylureidomethyl, N-n-octylureidomethyl, N-isopropylureido, allylureido; substituted or unsubstituted arylureido C$_{0-5}$ alkyl, e.g., N-(ethylphenyl) ureidomethyl, N-(chlorophenyl) ureidomethyl, N-phenylureidomethyl, N-(dichlorophenyl) ureidomethyl, N-naphth-2-yl)ureidomethyl, N-thiazol-2-ylureidomethyl, N-thien-2-ylmethylureidomethyl, N-(fluorophenyl)ureido, N-(methoxyphenyl)ureido, and 2-(ethoxyphenyl)ureidomethyl; C$_{1-10}$ alkylcarbonylamino, e.g. t-butylcarbonylamino; alkanoylamidoalkyl, e.g. trimethylacetamidomethyl, carbomethoxyoctanoylamidomethyl, (isobutylphenyl) propionamidomethyl, 8-carboxyoctanoylamidomethyl, bromohexanoylamidomethyl, hydroxydodecanoyl amidomethyl, 4-nitrophenylprionamidomethyl, isopropylthioacetamidomethyl, benzyloxyacetamidomethyl, carbomethoxyacetamidomethyl, triphenylprionamidomethyl, cyclohexylacetamidomethyl, methylcyclohexane carboxamidomethyl, (3-hydroxy-4,4,4-trichlorobutyramido)methyl, and phenylthioacetamidomethyl; thioether, e.g. C$_{1-8}$ alkylthio, phenylthio, and C$_{1-8}$ alkylthio substituted with phenyl; ethers, e.g. n-butyloxy, ethylene ketal; substituted and unsubstituted aryl ethers such as thiophenoxy, biphenyloxy, (3-pyridyl) oxy, chlorophenyloxy, methylphenyloxy, phenyloxy, methylsulfonylphenyloxy, pyrimidinyloxy; and the like.

Procedures for synthesizing compounds of structural formula (I) with various substituents at the 16- and 17-position are known in the art. The desired substitution at the 16- or 17-position may be effected before conducting the stereoselective reduction of the present invention, or alternatively, some other substituent, such as hydroxyl or protected hydroxyl may be present at the 16 or 17-substituent during the stereoselective reduction of the present invention, and subsequent to the reduction, the desired substitution may be effected on the D ring of the azasteroid.

Procedures for making ether and thioether substituents in the 17-position are described in U.S. Pat. No. 5,091,534, and PCT Publications WO 93/23041 corresponding to U.S. Pat. No. 5,610,162 and WO 93/23040 corresponding to U.S. Pat. No. 5,536,727. 17-Anilide derivatives are described, for example, in PCT publication WO 94/07861 and EP 0 663 924, and unsubstituted, monosubstituted or disubstituted amide derivatives in the 17-position are described in PCT publications WO 93/23038, WO 93/23051, corresponding to U.S. Pat. No. 5,510,485 WO 93/23420, and U.S. Pat. Nos. 4,220,775; 4,760,071; 4,845,104; 5,237,067; 5,091,380; 5,061,801; 5,215,894. 17-oxo-derivatives are described in U.S. Pat. Nos. 4,220,775; 4,377,584 and 17-hydroxy derivatives are described in U.S. Pat. Nos. 4,220,775; 4,377,584. Cyano derivatives at position 17 are described in U.S. Pat. No. 4,220,775 and 17-tetrazolyl analogs are described in U.S. Pat. No. 4,220,775. 17-arylalkylcarbonyloxy alkyl derivatives, 17-cycloalkylarylcarbonyloxy alkyl derivatives, and 17-benzoyloxyalkyl derivatives are described in U.S. Pat. No. 4,377,584. 17-acyl, substituted or unsubstituted derivatives are described in U.S. Pat. Nos. 5,049,562; 5,138,063; 5,151,429; 5,237,061; 5,120,742; 5,162,332; 5,061,802; 5,098,908; 5,196,411; 5,075,450; 5,061,803; 5,324,734; 17-thiobenzoyl are described in U.S. Pat. No. 5,151,430; and 17-polyaroyl derivatives are described in U.S. Pat. No. 5,162,322. Particular 17-alkyl derivatives, either substituted or unsubstituted, are described in PCT publications WO 93/23050, corresponding to U.S. Pat. No. 5,510,351 WO 93/23419, corresponding to U.S. Pat. No. 5,527,807, WO 93/23051 corresponding to U.S. Pat. No. 5,510,485 and WO 95/00147 corresponding to U.S. Ser. No. 08/537,876 (allowed) and 17-urea, thiourea, carbamate and thiocarbamate derivatives are described in PCT publications WO 93/23048 corresponding to U.S. Ser. No. 08/338,574 (allowed) now U.S. Pat. No. 5,620,986; and 95/12398.

Procedures for substituting at position 16 with: lower alkyl is described in PCT publication 93/23039, to U.S. Ser. No. 08/338,571 (allowed) and U.S. Pat. Nos. 5,049,562; 5,138,063; 5,278,159; and 4,377,584, and hydroxyl is described in U.S. Pat. Nos. 5,278,159 and 4,377,584. Procedures for further substitution at position 17 are described in: PCT publication WO 95/11254.

Procedures for the formation of a 7-β bond are described in U.S. Pat. No. 5,237,064.

The term "alkyl" includes both straight and branched chain alkyl groups, and unless otherwise specified "aryl" includes phenyl, pyridinyl and pyrimidinyl.

Hydroxy and amino protecting groups are known to those of ordinary skill in the art, and any such groups may be used. For example, acetate, benzoate, ether and silyl protecting groups are suitable hydroxy protecting groups. Standard silyl protecting groups have the general formula —Si(Xa)$_3$, wherein each Xa group is independently an alkyl or aryl group, and include, e.g. trimethylsilyl, tri-ethylsilyl, tri-i-propylsilyl, triphenylsilyl as well as t-butyl-di-(Xb)-silyl where Xb is methyl, ethyl, isopropyl or phenyl (Ph). Standard amino protecting groups have the general formula —C(O)—Xc, wherein Xc is alkyl, aryl, O-alkyl or O-aryl, and include, e.g. N-t-butoxycarbonyl. See also *Protective*

*Groups in Organic Synthesis*, T. W. Green et al. (John Wiley and Sons, 1991) for descriptions of protecting groups.

One class of the process of the present invention comprises the reduction of a Δ-5 steroidal enelactams of formula I:

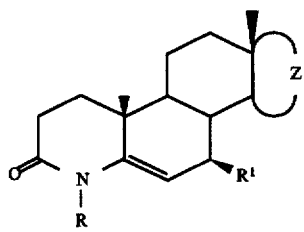

wherein:

Z is

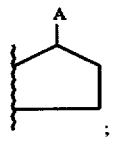

R is selected from H and $C_{1-5}$ alkyl;
$R^1$ is selected from $C_{1-5}$ alkyl and phenyl;
and A is any synthetically feasible substituent.

In a sub-class of this class of the invention, A is selected from carboxyl and hydroxyl. In a preferred embodiment of this subclass, R is selected from H and methyl and $R^1$ is methyl.

In yet another sub-class of this class of the invention, R is selected from H and methyl, $R^1$ is methyl, and A is $C_{1-10}$ alkyl. In a preferred embodiment of this subclass, A is 6-methylhept-2-yl.

Another class of the process of the present invention comprises the reduction of a Δ-5 steroidal enelactams of formula I:

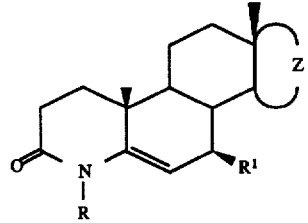

wherein:

Z is

R is selected from H and $C_{1-5}$ alkyl;
$R^1$ is selected from $C_{1-5}$ alkyl and phenyl;
and A is any synthetically feasible substituent.

In a sub-class of this class of the invention, A is selected from keto, hydroxyl, and protected hydroxyl. In a preferred embodiment of this subclass, R is selected from H and methyl and $R^1$ is methyl.

In yet another sub-class of this class of the invention, A is selected from ether and aryl ether. In a preferred embodiment of this subclass, R is selected from H and methyl. Most preferably, $R^1$ is methyl.

Compounds of formula I are useful for making 7β-methyl substituted 4-azasteroid compounds, and particularly those which are inhibitors of 5α-reductase. Examples of such compounds include but are not limited to those disclosed in U.S. Pat. Nos. 4,377,584 and 4,760,071; WO 93/23419 corresponding to U.S. Pat. No. 5,527,807; WO 93/23420; and WO 95/11254. More particularly, compounds that can be made from an intermediate of formula I in which Z is

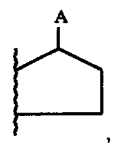

and A is 6-methylhept-2-yl include those of general Formula IV:

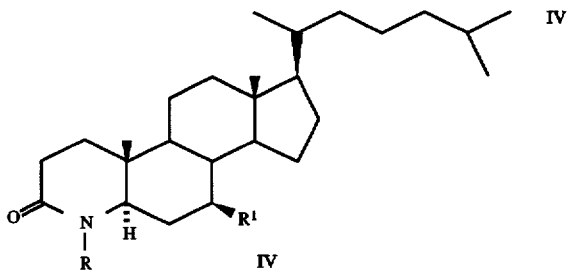

Synthesis of enelactams of formula I is described in U.S. Pat. No. 5,237,064. An exemplary synthetic scheme showing how to make enelactams of formula I and their subsequent reduction to compounds of formula II, compounds 8 and 9, is as follows:

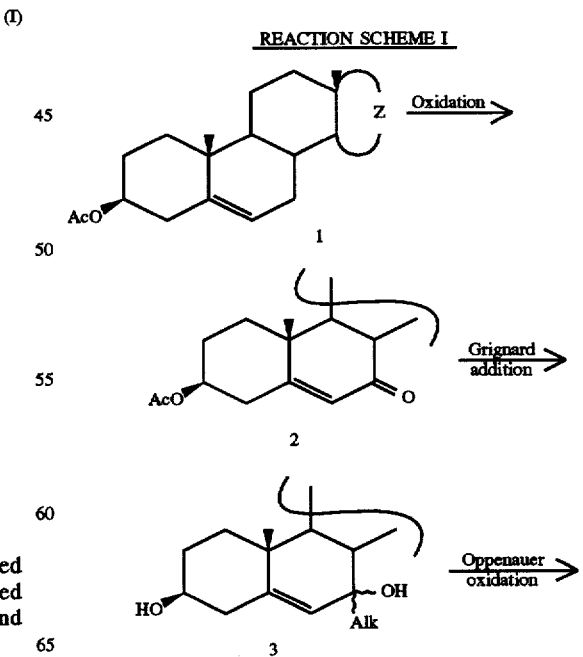

-continued
REACTION SCHEME I

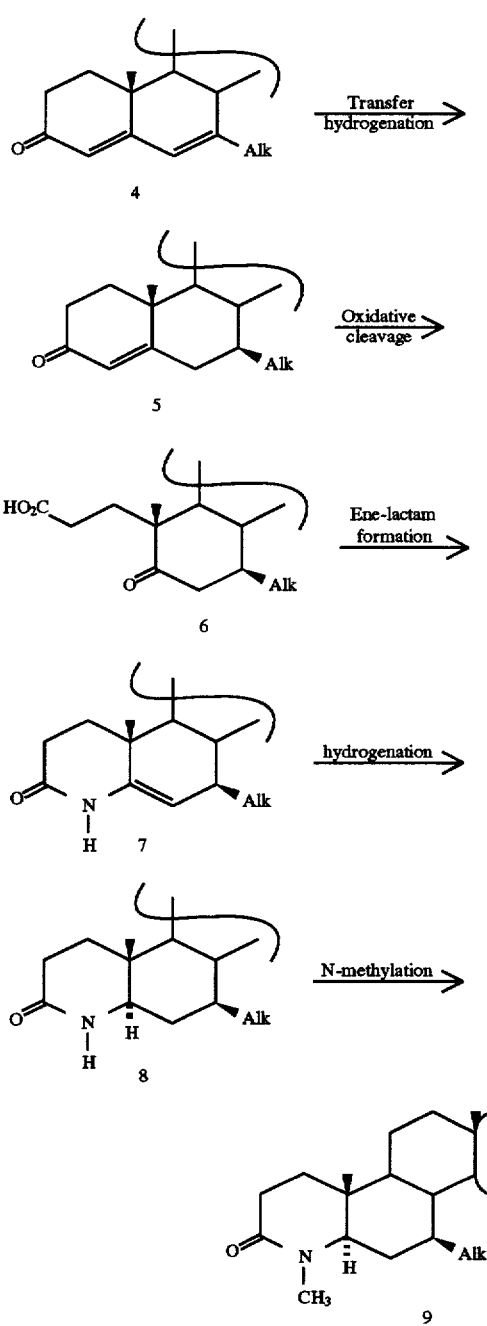

The starting materials for the process generally are the 3-acetoxy-androst-5-enes which are known and available in the art.

As shown in the above Reaction Scheme, the "Alk" substituent can be introduced onto the B ring of the 4-aza steroid generally by the application of an organometallic carbonyl addition reaction, e.g., the Grignard reaction in which the 7-carbonyl group can be reacted with the Grignard reagent containing "Alk" as the R radical in RMgX. The Grignard reaction conditions are conventional and include the use of, e.g., methyl, allyl or cycloalkyl magnesium chloride, ethyl magnesium bromide, cyclopropyl magnesium bromide, and the like. Preferably, the Grignard reagent is used with $CeCl_3$. Usable dry solvents include, e.g., tetrahydrofuran (THF), diethyl ether, dimethoxyethane, and di-n-butyl ether. The reaction is conducted under dry conditions generally in the temperature range of 0° C. to 40° C. Generally, the reaction requires about 6 to 24 hours for completion. Other organometallic carbonyl addition reactions can be used in this step, such as those utilizing lithium and zinc organometallic reagents which are known in the art. "Alk" is $C_{1-5}$ alkyl or phenyl, preferably methyl, ethyl, butyl or phenyl.

The adduct 3 is then oxidized with e.g., aluminum isopropoxide and cyclohexanone (Oppenauer oxidation conditions) in, e.g., refluxing toluene solvent to produce the 7-substituted-4,6-dien-3-one 4. Other reagents which can be used are, e.g., aluminum ethoxide or aluminum t-butoxide. Other solvents which can be used include, e.g., methylethylketone (MEK) and xylene. The temperature is generally in the range of about 60° to 120° C., and the reaction is carried out under anhydrous conditions and generally requires about 2 to 24 hours for completion.

The dien-3-one 4 is next converted to the 4-ene 5 by treatment with Pd on carbon, DBU (1,8-diazabicyclo[5.4.0] undecene-7, and cyclohexene in a solvent such as ethanol.

The A Ring is next cleaved by treatment with, e.g., potassium permanganate, sodium periodate in, e.g., t-butylalcohol at 80° C. to produce the corresponding seco-acid 6. Other oxidation reagents which can be used include ruthenium tetraoxide and ozone. Other solvents which can be used are: $CH_3CN$, $CCl_4$, methanol (MeOH) and $CH_2Cl_2$. The reaction generally requires about 2 to 4 hours to proceed to completion.

The seco-acid in a $C_{2-4}$ alkanoic acid such as acetic acid (HOAc) is treated with ammonium acetate at about 15°–30° C. followed by warming to reflux for about 2 to 4 hours. After cooling to about 50°–70° C., water is added and the mixture seeded to cause crystallization of the ene-lactam 7.

Hydrogenation of the ene-lactam to selectively obtain the 5α or 5β-reduction product is accomplished described above and in the examples that follow.

If an N-alkyl compound of formula II is desired, lactam 8 may be N-alkylated as illustrated in Example 2. Alternatively, an N-alkylated enelactam of formula I prepared according to the methods outlined in U.S. Pat. No. 5,237,064, may be directly reduced by the process of this invention as illustrated in Example 3.

Both the 4-N-alkyl and the 4-NH enelactams are unstable in air and the solvent should be degassed prior to dissolving the enelactam and subsequent reduction. In the case of the 4-NH enelactam, an amount of BHT (butylated hydroxy toluene) corresponding to 0.2% of the starting material should also be added to the solvent before dissolving the enelactam.

Representative experimental procedures utilizing the novel process are detailed below. These procedures are exemplary only and should not be construed as being limitations on the novel process of this invention.

EXAMPLE 1

Preparation of 7β-methyl-4-aza-5α-cholestan-3-one

Step 1:

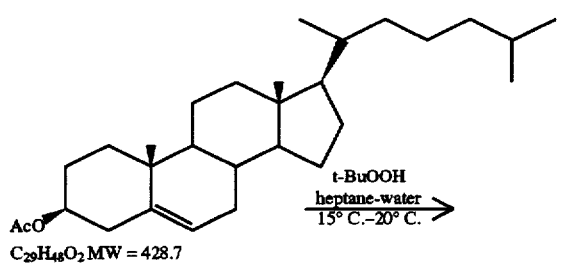

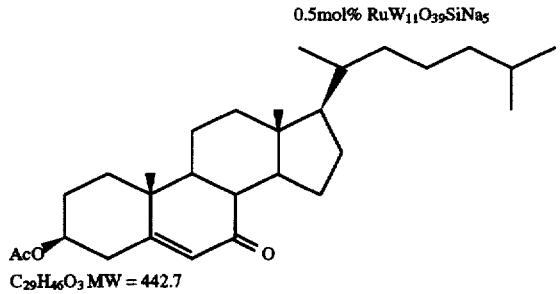

| Materials | Amt | Mole | MW |
|---|---|---|---|
| Cholesteryl acetate (95% Aldrich) | 78.1 g | 0.173 | 428.7 |
| t-BuOOH (70 wt %, Aldrich) | 189 g | 1.46 | 90.12 |
| $Na_2WO_4 \cdot 2H_2O$ | 3.3 g | 0.010 | 329.9 |
| $RuCl_3 \cdot xH_2O$ | 0.24 g | 0.00116 | 207.43 |
| Sodium metasilicate ($Na_2SiO_3$) | 0.315 g | 0.00258 | 122.06 |
| Sulfuric acid (d = 1.84 g/mL, 18 M) | 0.45 mL | 0.0081 | 98.08 |
| Sodium sulfite ($Na_2SO_3$) | 39 g | 0.309 | 126.04 |
| heptane | 300 mL | | |
| MEK (methyl ethyl ketone) | 550 mL | | |
| water | 460 mL | | |

In a 2000 mL 3-necked flask was added sodium tungstate dihydrate (3.3 g), sodium metasilicate (0.315 g) and 70 mL water and stirred until homogeneous. The solution was neutralized (pH=6–7) with concentrated sulfuric acid (0.45 mL). A 4° C. exotherm was noted for the addition of acid. Ruthenium trichloride hydrate (240 mg) was added and the mixture stirred for 10 min. Cholesteryl acetate (78.1 g) and heptane (300 mL) were added to the catalyst mixture. The stirring rate was 225–275 rpm with an overhead paddle stirrer.

70% t-BuOOH (189 g) was added over 5–10 min. An internal temperature of 15°–20° C. was maintained by cooling with a water bath. The temperature of the batch began to rise slowly after an induction period of 5–15 min. The reaction was stirred until less than 1.5 wt % of s.m. (starting material) and less than 2% of the 7-hydroxy cholesteryl acetate intermediate remained, about 20–24 hrs.

The reaction was monitored with a YMC basic column, 90:10 acetonitrile:water, flow rate=1.5 mL/min, UV detection at 200 nm. Retention times: $t_R$ cholesteryl acetate=17.0 min, $t_R$ 7-keto cholesteryl acetate=7.8 min, $t_R$ enedione 4.5 min, $t_R$ 7-hydroperoxides, 7-ols intermediates=6.8, 6.9, 7.0, 8.2 min. Later eluting impurities at 18 and 19 min are the 7-t-BuOO-cholesteryl acetates.

To the reaction mixture was added 550 mL MEK, 390 mL water, and 39 g sodium sulfite. The mixture was heated to 70° C. until the enedione impurity was gone, about 3 hrs. The reaction mixture cooled, then was transferred to a separatory funnel and the aqueous layer cut and then the organic layer washed with 100 mL 1% brine. The MEK and t-BuOH were then removed by an azeotropic distillation with heptane (800 mL heptane added after an initial concentration to 300 mL) until less than 0.7% combined MEK and t-BuOH remained as assayed by GC (gas chromatography).

The heptane was checked for MEK and tBuOH levels by GC using an HP-5 column at 35° C. with a 0.5 mL flow rate. $t_R$ MEK=4.9 min, $t_R$ tBuOH=5.3 min, $t_R$ heptane=7.7 min. The volume was adjusted to 350 mL, cooled to −5° C. and filtered, washing twice with 150 mL 0° C. heptane. After drying, the product was obtained as an off-white solid. Melting point (m.p.): 155°–157° C. NMR ($^1H$, 300 MHz, $CDCl_3$): 5.70 (s, 1H), 4.7 (m, 1H), 2.5–0.8 (m, 43H), 0.6 (s, 3H).

Step 2:

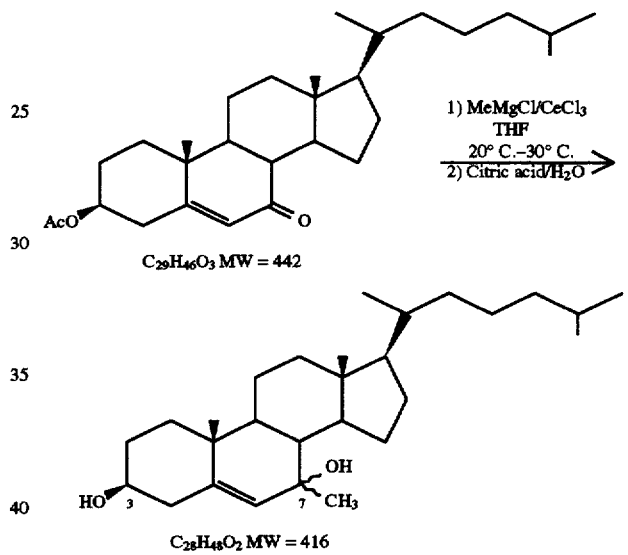

| Materials | Amt | Mole | MW |
|---|---|---|---|
| 7-keto-cholesteryl acetate (95% pure) | 60 g (as is) | 0.13 | 442 |
| Methyl magnesium chloride (3.0M) | 160 mL | 0.48 | |
| $CeCl_3$ (anhydrous) | 16.6 g | 0.068 | 245 |
| THF (KF = 50 µg/mL) | 300 mL | | |
| Citric acid | 115 g | 0.60 | 192 |
| water | 500 mL | | |
| toluene | 600 mL | | |
| sat'd $NaHCO_3$ | 240 mL | | |

Anhydrous cerium chloride (16.6 g) was stirred as a slurry in THF (150 mL) at 20° C. under $N_2$ for 2 h. After two hours a sample of the slurry was removed and showed fine needles under a microscope. To the slurry was added the Grignard reagent (160 mL) and the resulting light purple mixture was aged for 30 minutes.

To the cooled mixture (20° C.) was added the ketone (60 g at 95% purity, 57 g by assay) in THF (150 mL) over 50 minutes while allowing the mixture to exotherm to 30° C. Addition of the ketone to the Grignard reagent was exothermic, the exotherm was controlled by the rate of addition. The ketone solution in THF should be warmed to 30° C. to ensure complete dissolution, prior to adding it to the Grignard reagent.

The reaction progress was monitored by HPLC (high pressure liquid chromatography). A 0.5 mL sample was added to 10 mL of 0.1N HOAc and then diluted to 50 mL with CH₃CN. HPLC conditions [Zorbax® phenyl column, CH₃CN, water, phosphoric acid; 75:25:0.1 gradient elution to 90:10:0.1 at 18 minutes, flow=1.5 mL/min, UV detection at 200 nm]. Retention times, 3,7-diol $t_R$=5.6 and 5.9 min, starting ketone $t_R$=10.9 min, intermediate 7-OH, 3-OAc $t_R$=9.8 and 10.8 min.).

Once complete, the reaction was quenched by adding it to a 0° C. mixture of citric acid solution (115 g in 300 mL of water) and toluene (300 mL). The quench was exothermic. (NOTE: The rate of addition should be carefully controlled to maintain an internal temperature below 10° C.)

The two phase mixture was stirred for 30 minutes and allowed to stand for 10–15 minutes for an adequate phase separation. The pH of the aqueous layer was ca. 2. The organic phase was separated, washed with water (200 mL, pH=3 after washing) and saturated NaHCO₃ solution (240 mL, pH=8 after washing). This afforded 750 mL of an organic layer which contained 66 mg/mL of diol.

The batch was concentrated to 300 mL in vacuo (100–200 mm), diluted to 600 mL with toluene and re-concentrated to 360 mL. The solvent switch to toluene was considered complete when the G.C. area % of THF was <2% of the toluene area %. (NOTE: The first 200 mL of the distillation has a tendency to foam at low pressures. Once this phase is complete, the vacuum should be brought down to 100 mm. The distillation temperature slowly rises from 20° C. to ca. 45° C. as the solvent switch to toluene nears completion.)

Samples of the distillate were assayed for residual THF using G.C. A sample of ca. 0.1 mL was diluted to 1 mL with methanol. G.C. conditions: [HP-5 column (25M, 0.32 μm ID) using a heated block injector, 35° C. isothermal, flow= 0.5 mL/min], MeOH $t_R$=5.5 min, THF $t_R$=6.2 min, toluene $t_R$=10.1 min. The final assay was performed using a sample from the batch.

The organic layer contained 134.4 mg/mL of diols. (NOTE: The KF of the batch should be below 100 μg/mL before proceeding with the next step.)

Step 3: Oppenauer Oxidation

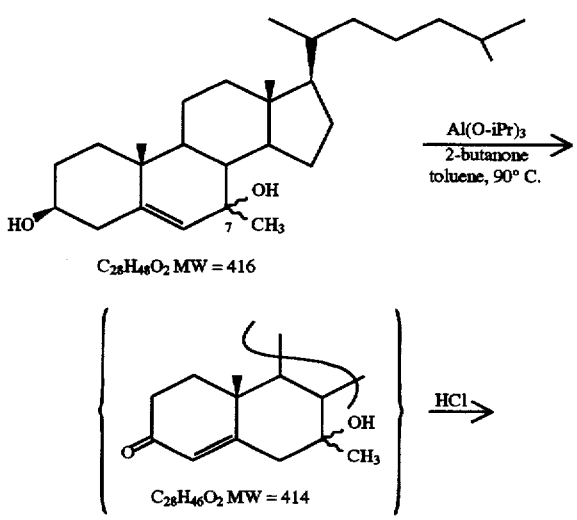

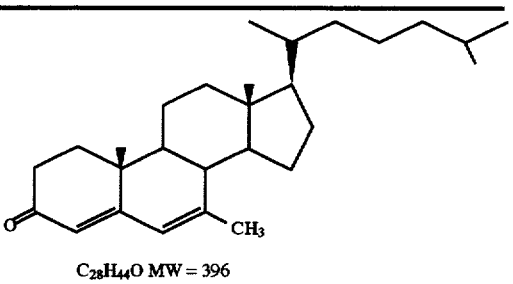

$C_{28}H_{44}O$ MW = 396

| Materials | Amt | MMole | MW |
|---|---|---|---|
| 7-methyl-7-hydroxy-cholesterol | 30.2 g | 72.6 | 416 |
| 2-butanone (d = 0.805, F = 480 μg/mL) | 126 mL | 1404 | 72.11 |
| Aluminum isopropoxide | 18.9 g | 93 | |
| | 204.25 | | |
| 3N HCl | 120 mL | | |
| 5% NaCl solution | 120 mL | | |
| Conc. HCl | 3.5 mL | 42 | |
| D.I. water | 60 mL | | |
| Saturated NaHCO₃ | 60 mL | | |

To the toluene solution of the diol (256 mL, 118 mg/mL) was added 2-butanone (126 mL) and aluminum isopropoxide (18.9 g). The solution was heated to reflux (92° C.) under nitrogen. The reaction progress was monitored by HPLC.

The batch was assayed for 2-butanone content by G.C. prior to adding the aluminum isopropoxide. A sample of ca. 0.1 mL was diluted to 1 mL with MeOH. G.C. conditions [HP-5 column (25 m, 0.32 μm ID) using a heated block injector at 250° C., column temp at 35° C. isothermal, flow=0.5 mL/min] 2-butanone $t_R$=6.1 min, MeOH $t_R$=5.5 min, toluene $t_R$=10.1 min. The KF of the starting mixture was 70 μg/mL.

A 0.1 mL sample of the reaction mixture was quenched into 0.1N HOAc solution (2–3 mL) and then diluted to 10 mL with CH₃CN in a volumetric flask. HPLC conditions [25 cm Zorbax® Phenyl column; CH₃CN:H₂O with 0.1% phosphoric acid: 75:25 gradient elution to 90:10 at 18 min, hold 90:10 until 22 min; flow=1.5 mL/min, UV detection at 210 nm.] Starting diols $t_R$=5.4, 5.8 min, intermediate Δ-4 eneone $t_R$=6.4 min, dieneone $t_R$=12.1 min.

The reaction was considered complete when the level of starting diol was <3 area % (8 hours). Once complete the batch was cooled to 15°–20° C. and quenched with 3N HCl (120 mL). The two phase mixture was stirred for 20 min, and then allowed to settle. The lower aqueous layer was removed and the organic layer was washed with 5% NaCl (120 mL). The batch was concentrated in vacuo to one half volume (40°–60° C. at 150 mm). The distillation removed excess 2-butanone from the batch. The level of 2-butanone in the final batch was <2% of the toluene (using G.C.) and the KF was 60 μg/mL.

The toluene solution was treated with conc. HCl (3.5 mL) at 25° C., under N₂. The reaction was assayed by HPLC until the intermediate tertiary alcohol was completely converted to dieneone (about 1 h). The solution was washed with D.I. water (60 mL) and saturated NaHCO₃ (60 mL). The pH of the bicarbonate wash was 8.5. (NOTE: The decomposition reaction will turn black if run for longer than 8 hours.) The resulting red solution (128 mL) contained 202 mg/mL of dieneone.

Step 4: Transfer Hydrogenation

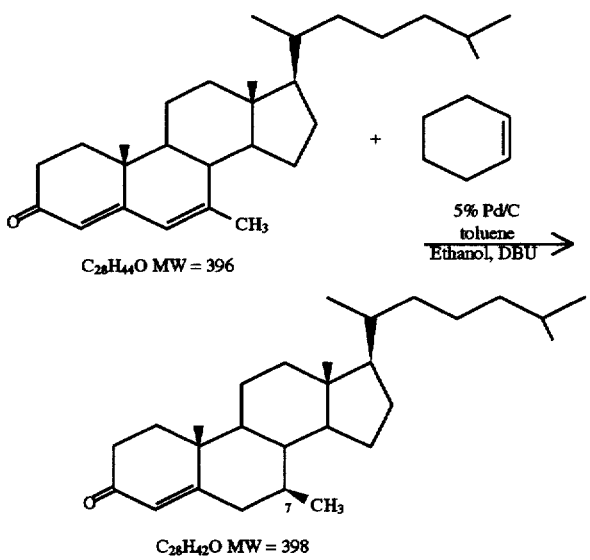

C₂₈H₄₄O MW = 396

C₂₈H₄₂O MW = 398

| Materials | Amt | MMole | MW |
|---|---|---|---|
| Dieneone (toluene solution) | 31.5 g | 79.5 | 396.7 |
| 5% Palladium on carbon (dry) | 4.5 g | | |
| Cyclohexene (d = 0.811) | 120 mL | 1.18 mole | 82.15 |
| 1,8 diazabicyclo[5.4.0]undec-7-ene (DBU) | 0.63 mL | 4.2 | 152.2 |
| Absolute ethanol | 495 mL | | |
| 3N HCl | 150 mL | | |
| half saturated NaHCO₃ | 100 mL | | |
| Solka Floc ™ diatomaceous earth | 250 mL | | |
| Hexanes | | | |
| t-butanol | 175 mL | | |

The toluene solution of the dieneone (150 mL at 214.6 mg/mL) was diluted with ethanol (120 mL) and cyclohexene (120 mL) and DBU (0.62 mL). To the mixture was added 5% palladium on carbon (9.0 g of 50% water wet). The mixture was degassed using vacuum/nitrogen purges (3×). The slurry was the heated to reflux (reflux temperature=72° C.). The reaction was monitored by HPLC.

A 2 mL sample of the reaction mixture was filtered through Solka Floc™ diatomaceous earth. The filtrate (0.1 mL) was diluted to 10 mL with CH₃CN and analyzed by HPLC: 25 cm Zorbax® phenyl column; acetonitrile/water containing 0.1% phosphoric acid: gradient elution from 75:25 to 90:10 CH₃CN: water in 18 min, hold 90:10 until 22 min; flow=1.5 mL/min; UV detection at 200 nm.

Dienone $t_R$=12.1 min, Δ-4 enone $t_R$=13.2 min, Δ-5 enone $t_R$=14.1 min, over-reduced ketone $t_R$=14.4 min, ethyl enol ether $t_R$=20.9 min. The over-reduced ketone should be assayed at 192 nm.

The reaction was considered complete when the dieneone level was <2 A % and the Δ-5 enone level was 5% (about 10 hours). When the reaction was complete the mixture was cooled to ambient temperature. The palladium was removed by filtration through Solka Floc™ diatomaceous earth and the filter cake was washed with ethanol (150 mL).

The batch contained 51 mg/mL of enone. (NOTE: Prolonged reaction times should be avoided since over-reduction can occur. If the starting material has been consumed and the level of Δ-5 enone is >5% after 10 hours, then the palladium should be filtered, and the isomerization completed without catalyst present.)

The solution was concentrated under reduced pressure (75 mm) to a volume of approximately 150 mL. The batch was diluted with ethanol (225 mL) and re-concentrated to 150 mL.

The solvent switch to ethanol was considered complete when the toluene level was <2% of the ethanol by G.C., and there was no detectable cyclohexene. (NOTE: Removal of cyclohexene is important since it reacts in the subsequent oxidative cleavage step and unproductively consumes periodate.) A 0.1 mL sample was diluted to 1 mL with ethanol for the cyclohexene assay (and 1,1,1 trichloroethane for the toluene assay). G.C. conditions [HP-5 (25M× 0.32 μm ID), using a heated block injector at 250° C., column temp at 35° C. isothermal, flow=0.5 mL/min] ethanol $t_R$=5.6 min, cyclohexene $t_R$=7.7 min, trichloroethane $t_R$=7.7 min, toluene $t_R$=10.2 min. The presence of cyclohexene is also detectable by ¹H NMR (CDCl₃) of the solution: cyclohexene vinyl protons at δ=5.64 ppm, eneone vinyl proton at δ=5.69 ppm.

The concentrate was diluted with hexanes (250 mL) and 3N HCl (150 mL). The two phase mixture was warmed to 40° C. until enol ether hydrolysis was complete. The layers were separated and the organic layer was washed with half saturated sodium bicarbonate (100 mL). The hexane phase had a volume of 291 mL, contained less than 5% ethanol by volume and assayed for 92 mg/mL of enone.

The solution was concentrated to 100 mL under reduced pressure (100 mm/15° C.). The batch was diluted with t-butanol (175 mL) and re-concentrated to 100 mL (100 mm/40° C.). The batch contained 260 mg/mL of the desired 7-β-methyl enone.

Step 5: Oxidative Cleavage

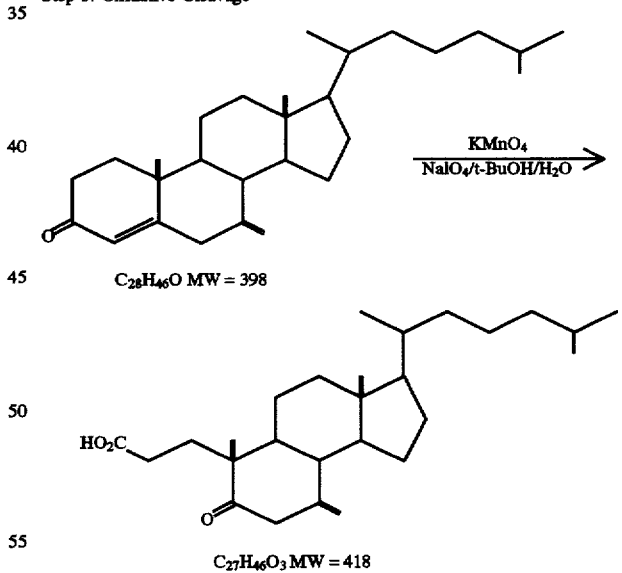

C₂₈H₄₆O MW = 398

C₂₇H₄₆O₃ MW = 418

| Materials | Amt | Mol | MW |
|---|---|---|---|
| 7-β-Methylcholest-4-ene-3-one | 300 g | 0.75 | 398 |
| t-Butanol (d = 0.786) | 6.6 L | | |
| Sodium carbonate | 159 g | 1.5 | 106 |
| Sodium periodate | 1550 g | 7.2 | 213.9 |
| Potassium permanganate | 11.1 g | 0.07 | 158 |
| D.I. Water | 14.2 L | | |
| Diatomite | 50 g | | |
| Ethyl acetate (d = 0.902) | 2.6 L | | |
| Heptane (d = 0.684) | 5.0 L | | |
| conc. Hydrochloric acid | 250 mL | | |

| | |
|---|---|
| 5% Aqueous NaCl | 2.5 L |
| Acetic acid (d = 1.049) | 9.0 L |

In a 5 L roundbottom flask was charged D.I. water (4.93 L), sodium periodate (1.55 Kg) and potassium permanganate (11.1 g). The slurry was stirred at 65° C. for 30 minutes to obtain complete solution.

To a solution of the enone (300 g) in t-butanol (4.60 L) was added a solution of sodium carbonate (159 g) in water (2.3 L). The two phase mixture was warmed to 65° C. The enone should be toluene, ethanol and cyclohexene free. (NOTE: Concentration of enone in organic layer is about 56 mgL$^{-1}$.) The sodium periodate solution was added to the enone solution over 3 h with rapid stirring, maintaining the reaction temperature at 65° C. The slurry was aged at 65° C. for 2 h. The periodate solution was added via a heated addition funnel.

Carbon dioxide gas was evolved during the reaction. A slow addition ensures controlled gas evolution. No exotherm was detected during addition. During the addition a purple/brown slurry was formed.

The reaction progress was monitored by HPLC. A 2 mL sample of the reaction mixture was cooled to 15° C. and filtered. The filtrate (0.1 mL) was diluted to 10 mL with water/CH$_3$CN (1:3). HPLC conditions [YMC Basic 25 cm×4.6 mm, CH$_3$CN, 0.01M H$_3$PO$_4$; 90:10 isocratic flow= 1.5 mL/min, UV detection at 200 nm]; enone t$_R$=11.5 min, seco-acid t$_R$=5.5 min.

The reaction was considered complete when the starting enone was <0.5 mg/mL. Water (3.0 L) was added and the slurry heated to reflux for 2 h to decompose any remaining KMnO$_4$ (color change from purple to brown) and to dissolve most of the solids precipitated on the vessel walls. The resultant slurry was cooled to 15° C. and filtered through dicalite (50 g). The vessel and cake were washed with t-butanol/water (1:2, 6.0 L).

The filter cake was assayed for seco acid by dissolving 200–400 mg of cake with 50 mL water and 50 mL acetonitrile then filtering into the sample vial through diatomite to remove the small amount of orange manganese solids. The filtrates (pH=9.0–10.5) were extracted with heptane (5.0 L).

Ethyl acetate (2.6 L) was added to the aqueous mixture and the pH adjusted to 2.5±0.3 by the addition of conc. HCl (250 mL). The aqueous layer was removed.

The organic layer was washed with 5% aqueous brine (2×1.2 L). The ethyl acetate solution was concentrated (150 mm.Hg, 30° C.) to approx 10% volume. Acetic acid (7.4 L) was added and the residual ethyl acetate removed by concentration (100 mm.Hg, 60° C.) to <1% by volume (<0.5 area % by HPLC). The final volume was adjusted to 5.0 L by addition of acetic acid. Ethyl acetate removal was monitored by HPLC using the conditions above except the flow rate was 0.5 mL min$^{-1}$ and UV detection at 210 nm. Ethyl acetate t$_R$=7.4 min, acetic acid t$_R$=6.9 min. The acetic acid solution was used directly in the following step (ene-lactam formation).

Step 6: NH-Enelactam Formation

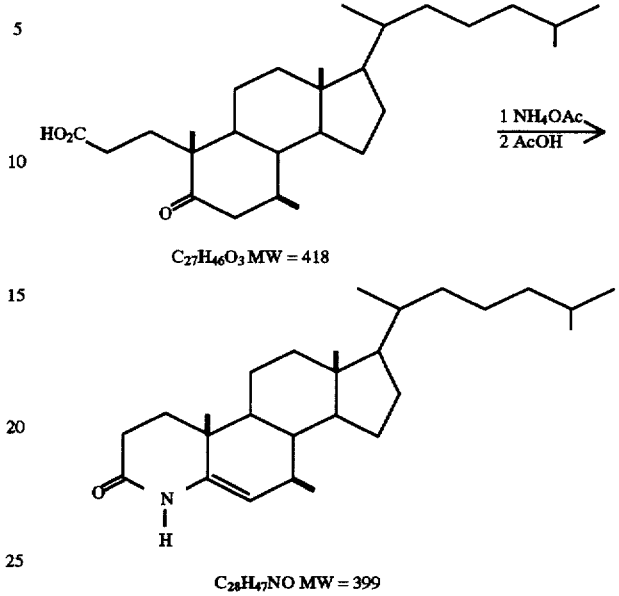

| Materials | Amt | Mole | MW |
|---|---|---|---|
| Seco-acid | 265 g | 0.634 | 418 |
| Ammonium Acetate | 488 g | 6.33 | 77.1 |
| 2,6-di-t-butyl-4-methylphenol (BHT) | 5.3 g | 0.024 | 220 |
| D.I. Water | 565 mL | | |
| Acetic acid | 833 mL | | |

To a solution of seco-acid in acetic acid (265 g in 5.3 L) obtained in the previous step was added BHT (5.3 g) and ammonium acetate (488 g) at 20° C. The slurry was warmed to a gentle reflux under a nitrogen atmosphere for 3 h. Complete solution was obtained at 30° C. The internal temperature was 120° C. at reflux. Color changed from yellow to dark red/brown. Use of reduced amounts of acetic acid results in oiling of the product at the crystallization stage.

The reaction progress was monitored by HPLC. HPLC conditions [SB Phenyl, CH$_3$CN, 0.01M H$_3$PO$_4$; isocratic 80:20 for 30 min, flow=1.5 mL/min, UV detection at 190/200 nm] Retention times: ene-lactam t$_R$=9.4 min, seco acid t$_R$=5.3 min. UV detection was at 190 nm for reaction progress and 200 nm for s.m. and product assay. The reaction was considered complete when <0.05 A % seco acid remained, about 3–4 hrs.

The reaction mixture was cooled to 60° C. and water (398 mL) added over 15 min. (NOTE: Addition of exactly 7.5% v/v water to the acetic acid solution is important.) The solution was allowed to cool to 50° C. and seeded with ene-lactam (1.0 g). Crystallization occurred at 50° C. The slurry obtained was aged at 50° C. for 1 h and then cooled to 0–2° C. over 2 h.

The slurry was filtered and the light tan solid washed with 5:1 acetic acid/water (1.0 L).

Step 7: NH-Enelactam Recrystallization

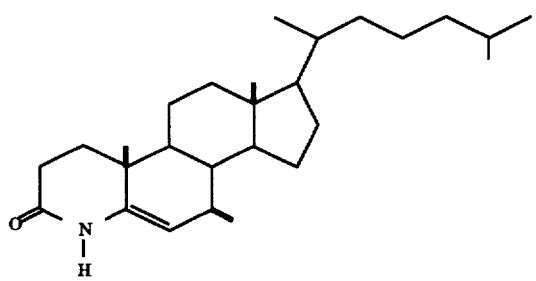

C₂₈H₄₇NO MW = 399

| Materials | Amt | Mole | MW |
|---|---|---|---|
| Enelactam | 20 g | 0.041 | 400 |
| D.I. Water | 17 mL | | |
| Acetic acid | 133 mL | | |
| BHT | 0.20 g | 0.00091 | 220 |

To 20 g at 83 wt % enelactam was added 100 mL acetic acid which contained 200 mg of BHT. The slurry was warmed to 60° C. under a nitrogen atmosphere to achieve dissolution, then cooled to 50° C. A charge of 10 mL water was then added. The mixture was then cooled to 5° C. over 1.5 hrs, aged for one hour and then the solid filtered off. (NOTE: The solution at 50° C. should have started crystallizing before cooling to 5° C.) The solution Kf after BHT addition was about 0.2–0.4% w/w.

The mother liquor amounts were monitored by HPLC. HPLC conditions [SB Phenyl, CH₃CN, 0.01M H₃PO₄; isocratic 80:20 for 30 min, flow=1.5 mL/min, UV detection at 200 nm] Retention times: ene-lactam t$_R$=9.4 min. Sample 100 μL and dilute to 10 mL with acetonitrile.

The slurry was filtered and the light tan solid washed with 5:1 acetic acid/water (40 mL) at 5° C.

M.p. solvate is 112°–115° C. Pure m.p. is 175°–178° C., softens at 162° C.

Step 8: N—H Enelactam Reduction

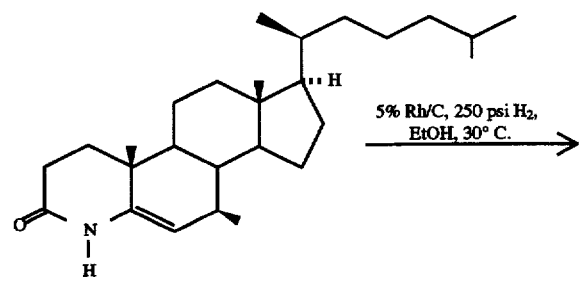

C₂₇H₄₅NO MW = 399.6

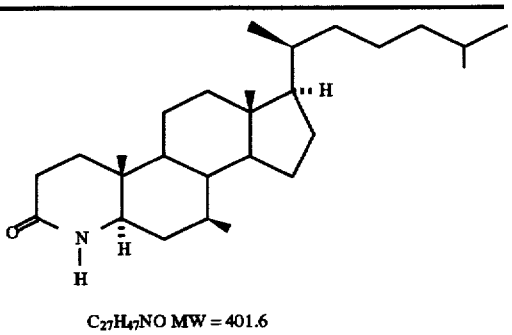

C₂₇H₄₇NO MW = 401.6

| Materials | Amount | Mol | MW |
|---|---|---|---|
| Enelactam | 1.02 g | .0026 | 339.6 |
| Ethanol(punctilious) | 100 mL | | |
| BHT | 2 mg | | |
| 5% Rhodium on carbon | 200 mg | .097 mmol | 103 |

BHT (2 mg) was dissolved in degassed ethanol (100 mL) and the solution degassed with nitrogen purge. The enelactam and 5% Rhodium on carbon (200 mg) were added and the slurry degassed for a further 30 minutes with stirring. The resultant slurry placed under 250 psi of hydrogen in a stirred autoclave maintained at 30° C. The reaction progress was monitored by HPLC. HPLC conditions [Zorbax® Phenyl, MeOH, H₂O; 90:10 isocratic, flow=1.0 mL/min, UV detection at 210 nm] ene-lactam t$_R$=min, 5-α lactam t$_R$=12.4 min, 5-β lactam t$_R$=15.0 min.

After 24 hours the mixture was removed from the hydrogenator and the catalyst filtered off. Analysis of the solution by HPLC shows a 1:264 mixture of 5-β:5-α product. The solution was concentrated to give the product as a white solid (m.p. 188°–190° C., 90% yield), 300 MHz NMR (H¹CDCl₃): 5.96(1H,brs), 3.05(1H,dd,J=12.3,3.5 hz), 2.38 (2H,m), 2.0(1H,m), 1.75(3H,m), 1.60–0.7(34H,m), 0.67 (3H.s); (C¹³CDCl₃) 172.2, 59.6, 56.8, 55.3, 52.0, 44.1, 42.6, 40.1, 39.5, 37.9, 36.2, 35.7, 35.2, 35.1, 33.6, 28.7, 28.6, 28.0, 27.8, 23.9, 23.0, 22.8, 22.6, 21.8, 18.9, 12.5, 11.5.

If an N-alkyl compound of formula II is desired, lactam 8 may be N-alkylated as illustrated by Example 2 shown below.

EXAMPLE 2

Methylation of 7β-methyl-4-aza-5α-cholestan-3-one

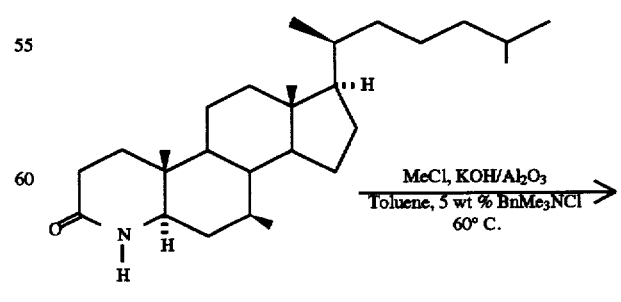

C₂₇H₄₇NO MW = 401.6

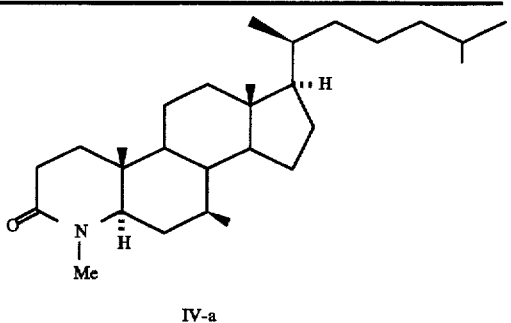

IV-a

C₂₈H₄₉NO MW = 415.7

| Materials | Amount | Mol | MW |
| --- | --- | --- | --- |
| N—H Lactam | 3.0 Kg | 7.47 | 401.6 |
| Methyl chloride | 453 g | 8.96 | 50.5 |
| KOH/Alumina[1:1] | 3.0 Kg | 22.8 | 56 |
| BnMe₃NCl | 150 g | 0.81 | 185.7 |
| Toluene (d = 0.867) | 14.0 L | | |

A 5 gallon autoclave was charged with a slurry of lactam (3.0 Kg), BnMe₃NCl (150 g) and potassium hydroxide on alumina (1:1, 3.0 Kg) in toluene (12 L) at room temperature. Methyl chloride (453 g) was introduced at 20° C. with slow stirring. The slurry was heated to 65° C. with slow stirring and aged for 1 h. An exotherm at 52° C. of about 3° C. was noted as a spike on the temperature recorder.

The reaction progress was monitored by HPLC. HPLC conditions [Zorbax® SB phenyl, CH₃CN, 0.01M H₃PO₄; 90:10 isocratic, flow=1.5 mL/min, UV detection at 200 nm] lactam $t_R$=12.4 min, IV-a $t_R$=15.0 min. 25 µL Sample of toluene layer was diluted to 2 mL with acetonitrile. The reaction was monitored until complete conversion was obtained (>99.95%). The reaction was complete in <60 min at 60° C.

The reaction mixture was cooled to 20° C. and purged with nitrogen (4×) to remove any excess MeCl. The toluene solution was filtered through Solka Floc™ diatomaceous earth (100 g) and the vessel and cake washed with toluene (2 L). The combined filtrates were concentrated at 100 mm. Hg and 20°–30° C. to a residual oil. The oil should be homogeneous in heptane (10 mLg-1) without any cloudiness.

The oil was assayed for toluene by G.C. oven temp 35° C. isothermal. The product (100 mg) was dissolved in methanol (0.5 mL) and 1 µL injected. Toluene $t_R$=4.4 min, methanol $t_R$=2.7 min.

The oil was kept under vacuum until the solvent level was <2%. The oil was poured into a glass tray and seeded with IV-a (1.25 g) and allowed to stand in vacuo (20 mm.Hg) overnight.

The resulting solid was cut into blocks and broken up in a WARING blender containing 2° C. water (10 L) to a particle size of <50 µm. The slurry was filtered, washed with water (5.0 L) and dried in a nitrogen stream overnight. Yield of product=3.0 kg, 97%.

The process of the present invention can also be used to directly reduce an N-alkylated enelactam of formula I as illustrated by Example 3.

EXAMPLE 3

Preparation of 4,7β-dimethyl-4-aza-5α-cholestan-3-one

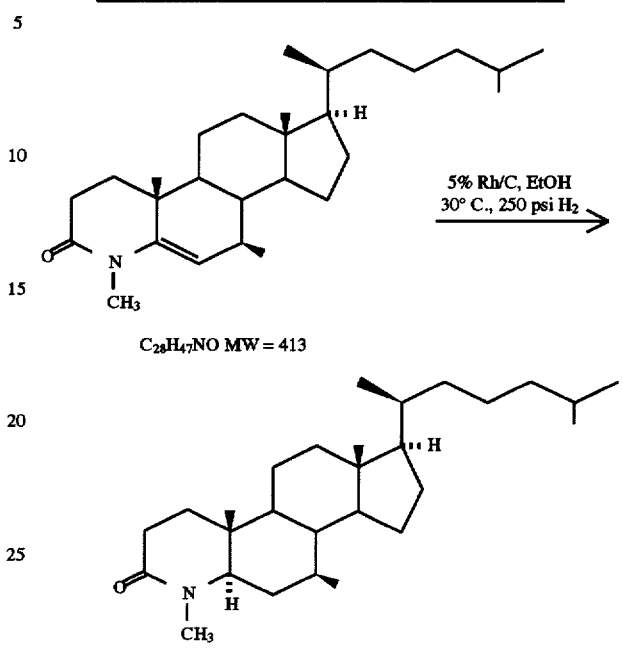

| Materials | Amount | Mol | MW |
| --- | --- | --- | --- |
| Enelactam | 1900.0 g | 4.75 | 399.64 |
| Ethanol(punctilious) | 22 L | | |
| 5% Rhodium on carbon | 380 g | 0.18 | 103 |
| Hydrogen | 250 psi | | |
| Celite | 100 g | | |
| Hexane | 4.0 L | | |

Enelactam (1900.0 g) was dissolved in ethanol (8.0 L) and the solution degassed with nitrogen purge for 18 h. 5% Rhodium on carbon (380 g) was added and the slurry degassed for a further 30 minutes with stirring. The resultant slurry was charged to a 5 gallon stirred autoclave.

A further charge of degassed ethanol (4.0 L) was used to rinse the starting material and catalyst into the autoclave. The hydrogenation was performed at 30° C. and 250 psi hydrogen pressure for 18 h. Typically <4% ene-lactam remains after 18 h.

The reaction progress was monitored by HPLC, [YMC-basic, CH₃CN, 0.1M H₃PO₄; 1.5 mL/min, λ=210 nm]. Retention times: Enelactam 16.1 min, trans-lactam 13.8 min, cis-lactam 13.1 min, 7-des methyl trans-lactam 12.4 min. Samples for HPLC analysis were removed without introducing oxygen into the system.

The hydrogenation mixture was filtered through Celite (100 g). Ethanol (8.0 L) was used to rinse the autoclave and wash the cake. The Celite was washed with ethanol (2000 mL).

The combined colorless filtrate was concentrated to residue at 75 mm. Hexane (4.0 L) was added, concentrated to residue and assayed for product. Analysis of the solution by HPLC shows a 1:500 mixture of 5-β:5-α product. The assay yield was 98%. The crude product contained unreacted ene-lactam (1.8%), 7-des methyl trans-lactam (<0.1%) and cis-lactam (<0.2%). The hydrogenation also produced 0.07% over-reduced product which lacks the lactam carbonyl oxygen.

The resulting oil was chromatographed on silica gel (17 kg, 230–400 mesh) eluting with 1:3 v/v ethyl acetate:hexane (100 L) followed by 3:1 v/v ethyl acetate:hexane (140 L). The fractions containing the 5α/β products were combined and concentrated under vacuum. The resultant oil was seeded with 5α product (1.0 g) and allowed to crystallize over 5 days. The resulting solid was ground in a mortar and pestle to give 4,7β-dimethyl-4-aza-5α-cholestan-3-one (1.53 Kg) as a white, low melting crystalline solid, m.p. 58°–62° C., 300 MHz $^1$H NMR (H$^1$CDCl$_3$): 3.02(1H, dd, J=12.7, 3.6), 2.92(3H, s), 2.43(2H, m), 2.01(1H, dt, J=12.3, 3.2), 1.92(1H, dt, J=12.7, 4.0), 1.89–1.70(3H,m), 1.58(1H, m), 1.52(1H,m), 1.41–0.96(17H, m), 1.05(3H, d, J=6.3), 0.92(3H, d, J=6.3), 0.87(3H, d, J=6.7), 0.86(3H, d, J=6.7), 0.84(3H, s), 0.81(1H, m), 0.68(3H, s), 75 MHz $^{13}$C NMR (C$^{13}$CDCl$_3$): 170.6, 64.7, 56.8, 55.2, 52.6, 44.0, 41.7, 40.1, 39.5, 36.1, 35.9, 35.8, 35.7, 33.1, 29.1, 28.6, 28.0, 27.7, 23.8, 23.2, 22.8, 22.5, 21.7, 18.8, 12.6, 12.4.

EXAMPLE 4

Preparation of 7β-methyl-4-aza-5β-cholestan-3-one

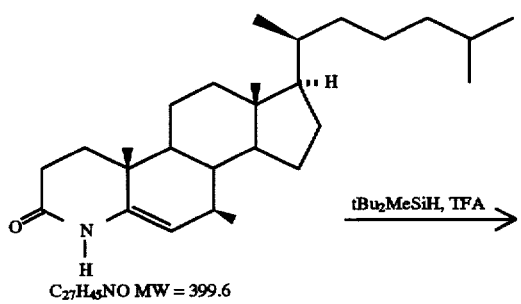

C$_{27}$H$_{45}$NO MW = 399.6

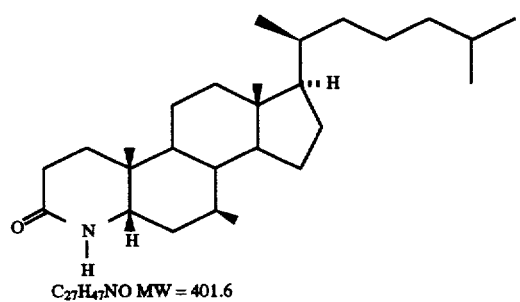

C$_{27}$H$_{47}$NO MW = 401.6

| Materials | Amount | Mol | MW |
|---|---|---|---|
| Enelactam | 333 mg | 0.83 mmol | 399.6 |
| Trifluoroacetic acid | 3 mL | | |
| Di-t-butylmethylsilane | 260 mg | | |

To 333 mg of enelactam (0.83 mmol) in 3 mL of trifluoroacetic acid was added 260 mg di-t-butylmethylsilane (1.64 mmol) and the mixture heated to reflux for about 2 hours until no enelactam remains. The mixture was cooled, concentrated to an oil, dissolved in hexane and washed with water twice.

Analysis of the mixture by HPLC showed a 90:1 ratio of 5-β:5-α product. Chromatography on silica using ethyl acetate gave the product as a white solid (m.p. 90°–94° C., 87% yield).

As in preparation of the α-reduction product, the process of this invention can be used to produce 5β-reduction products of N—H enelactams which can be subsequently N-alkylated as in Example 2 or to directly reduce N-alkylated enelactams as in Example 3.

EXAMPLE 5

Preparation of 4,7β-dimethyl-4-aza-5β-16β-hydroxy-androst-3-one

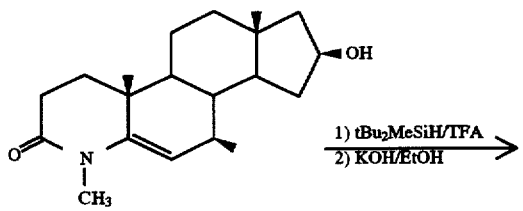

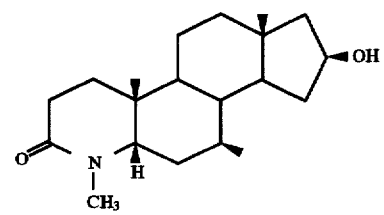

| Materials | Amt. | mmole | MW |
|---|---|---|---|
| Enelactam (100 wt %) | 2.0 g | 6.3 | 317.5 |
| TFA | 20 mL | | |
| Me(tBu)$_2$SiH | 5 g | 31.5 | 158 |
| EtOH | 20 mL | | |
| KOH | 1.76 g | 31.5 | 56 |

To the enelactam alcohol (2.0 g, 6.3 mmol) in TFA (20 mL) was added Me(tBu)$_2$SiH and heated to 60°–70° C. until less than 1% remained.

The reaction was monitored by HPLC. YMC-ODS-H80, CH$_3$CN:0.01% H$_3$PO$_4$: gradient elution from 60:40 to 90:10 in 15 minutes, flow=1.5 mL/min, UV detection at 210 nm. Enelactam-16-β-OH R$_T$=8.4 min, lactam-16-β-OH R$_T$=3.7 min, lactam-16-α-OH R$_T$=3.9 min intermediate trifluoroacetate, R$_T$=15.6 min.

The reaction mixture was cooled to RT and concentrated in vacuo. The oil was dissolved in 20 mL ethanol and 1M KOH (31 mL) added. The mixture was heated to 50° C. and aged until the trifluoroacetate was gone. After cooling to RT, 50 mL toluene was added and the layers separated. HPLC assay shows a 1:30 ratio of 5-α:5-β reduction isomers. The toluene layer was washed 2×50 mL water and then solvent switched to acetonitrile (10 mL), cooled to 0° C. and filtered off a white solid. 300 MHz $^1$H NMR(CDCl$_3$): 4.35 (1H, m), 3.0 (1H, dd, J=5.6, 2.8 Hz), 2.90 (3H, s), 2.4 (1H, br s), 2.3 (2H, m), 0.90–1.75(m, 25H). 75 MHz $^{13}$C NMR (CDCl$_3$): 171.1, 71.7, 64.9, 54.2, 50.7, 42.7, 41.3, 41.2, 40.2, 39.1, 34.6, 33.9, 31.7, 31.4, 31.0, 28.4, 22.2, 21.7, 21.4, 19.1.

EXAMPLE 6

Preparation of 7β-methyl-4-aza-5β-16β-phenoxy-androst-3-one

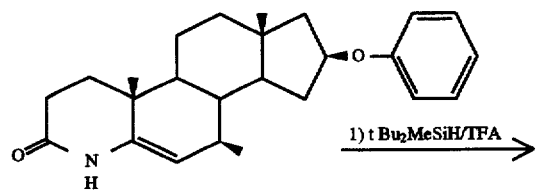

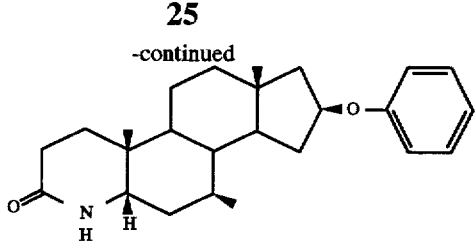

Starting with the enelactam above, the title compound is prepared according to the procedures of Example 4.

EXAMPLE 7

Preparation of 4,7β-dimethyl-4-aza-5β-16β-hydroxy-androst-3-one (Rhodium Hydrogenation)

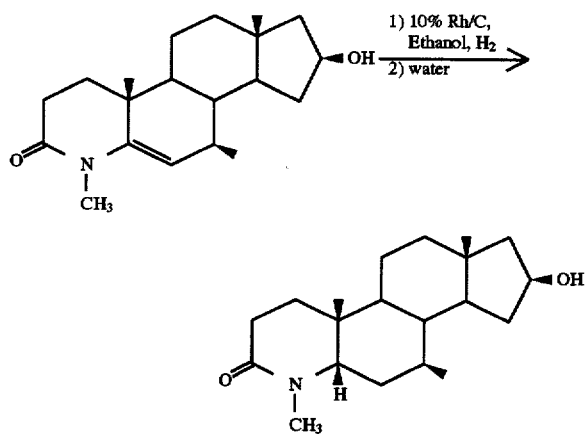

| Materials | Amt. | mmole | MW |
|---|---|---|---|
| Enelactam (100 wt %) | 1.150 g | 3.62 | 317.46 |
| 5% Rh/C | 0.640 g | | |
| 95% Ethanol | 17 mL | | |
| Solka Floc ™ diatomaceous earth | 5 g | | |
| DI water | 30 mL | | |

The enelactam alcohol (1.15 g) was dissolved in 95% ethanol (12 mL) and degassed with a nitrogen purge for 15 min. To this solution was added of 5 wt % Rh/C (0.64 g) and the slurry transferred to a stirred autoclave using 2.5 mL additional EtOH as a rinse. The mixture was placed under 40 psi hydrogen and heated to 30° C. for 4 h and then heated to 50° C. until <0.01% starting material remained.

The reaction was monitored by HPLC. SB phenyl CH₃CN:0.01% H₃PO₄: gradient elution from 45:55 for 10 min then gradient elution to 90:10 in 15 minutes, flow=1.5 mL/min, UV detection at 210. Enelactam-16-β-OH R_T=8.4 min, 5-b-lactam-16 β-OH R_T=3.7 min, 5-a-lactam-16-α-OH 3.9 min.

The batch was removed from the autoclave and cycled through a pad of Solka Floc™ diatomaceous earth until the rhodium was removed. An additional 15 mL of ethanol was used to wash the product from the filter cake. The combined filtrates were then re-filtered through a 0.2 µm in-line filter and concentrated to about 5 mL ethanol. HPLC assay shows a 250:1 ratio of 5-α:5-β reduction isomers. Water was slowly added until the cloud point was reached (20 mL), seeded with 10 mg lactam and aged 20 min. The slurry was then cooled to 0° C. and filtered. The product was obtained as a white solid. The filtrate and washes contains 3% of product.

300 MHz ¹H NMR(CDCl₁₃): 4.35 (1H, m), 3.0 (1H, dd, J=8.5, 3.2 Hz), 2.89 (3H, s), 2.4–2.2 (2H, m), 0.90–1.75(m, 25H). 75 MHz ¹³C NMR (CDCl₁₃): 170.9, 71.8, 64.8, 53.9, 52.7, 50.6, 41.7, 41.5, 40.7, 39.2, 36.0, 35.54, 35.50, 32.9, 29.3, 29.0, 22.9, 21.4, 19.5, 12.6.

EXAMPLE 8

Preparation of 4,7β-dimethyl-4-aza-5β-16β-phenoxy-androst-3-one

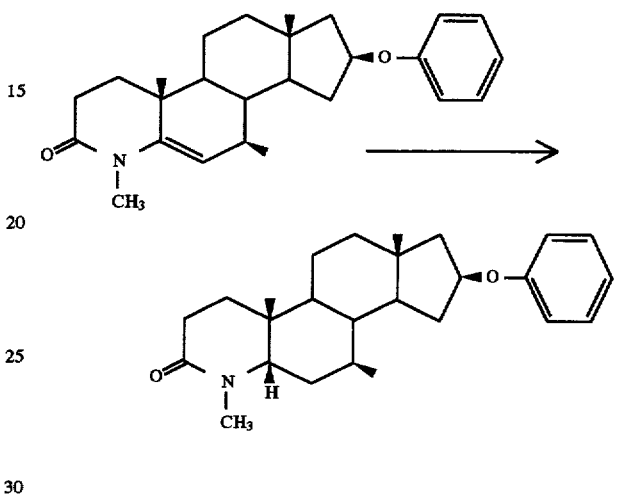

Starting with the 16-phenoxy-4,7b-dimethyl-4-aza-androst-5-en-3-one above and following the procedures of Example 4, the title compound is prepared.

EXAMPLE 9

According to the procedures outlined in Examples 1–8, the following compounds of structural formula below are prepared from the corresponding ene-lactam.

| Compound | R | R¹ | A |
|---|---|---|---|
| 30 | H | H | OH |
| 31 | Me | H | OH |
| 32 | Me | Me | OMe |
| 33 | H | Me | (—CH(CH₃)₂) |

EXAMPLE 10

According to the procedures outlined in Examples 1–8, the following compounds of structural formula below are prepared from the corresponding ene-lactams

EXAMPLE 11

According to the procedures outlined in Examples 1–8, the following compounds of structural formula below are prepared from the corresponding ene-lactams

| Compound | R | R¹ | A |
|---|---|---|---|
| 40 | H | H | OH |
| 41 | H | Me | O−CNHPh (O=) |
| 42 | Me | Me | −OMe |
| 43 | Me | Me | −O−phenyl |
| 44 | H | Me | −O−C₆H₄−CH₃ |
| 45 | Me | Me | −O−C₆H₄−Cl |

EXAMPLE 12

According to the procedures outlined in Examples 1–8, the following compounds of structural formula below are prepared from the corresponding ene-lactams

| Compound | R | R¹ | A |
|---|---|---|---|
| 50 | H | Me | −CH(CH₃)₂ |
| 51 | H | Me | −OH |
| 52 | Me | Me | −OMe |
| 53 | Me | Me | −OAc |
| 54 | H | Me | −CO₂H |

According to the procedures outlined in Examples 1–8, the following compounds of structural formula below are prepared from the corresponding ene-lactams

| Compound | R | R¹ | A |
|---|---|---|---|
| 60 | H | Me | 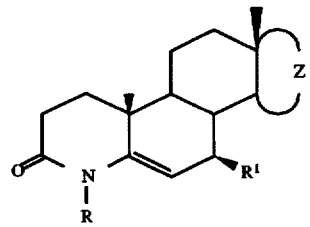 |
| 61 | Me | Me | 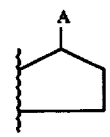 |
| 62 | H | Me | O−CNHPh (O=) |
| 63 | H | Me | −O−CH₃ |

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed:

1. A process for the stereoselective reduction of a Δ-5-4-aza-steroidal enelactam of the formula I:

(I)

wherein:

Z is

R is selected from H and $C_{1-5}$ alkyl;
R¹ is selected from $C_{1-5}$ alkyl; and
A is selected from:
(1) —H;
(2) protected hydroxy, wherein:
 protected hydroxy is selected from: dimethyl-t-butyl silyloxy, trimethylsilyloxy, tri-ethylsilyloxy, tri-isopropylsilyloxy, and triphenylsilyloxy;
(3) acetate;
(4) hydroxy;
(5) carboxy;
(6) protected amino, wherein:

protected amino is acetylamino;
(7) amino;
(8) $C_{1-10}$ alkyl;
(9) aryl-substituted $C_{1-10}$ alkyl, wherein:
   aryl substituted $C_{1-10}$ alkyl is omega-phenylpropyl;
(10) aryl, wherein:
   aryl is phenyl;
(11) substituted aryl, wherein:
   substituted aryl is phenyl, substituted with one to three substituents independently selected from:
   (a) —H,
   (b) —OH,
   (c) —CH$_3$,
   (d) —OCH$_3$,
   (e) —S(O)$_n$—CH$_3$, wherein n is selected from 0, 1, and 2,
   (f) —CF$_3$,
   (g) —CHO, and
   (h) —NHR$^7$, wherein R$^7$ is selected from: —H, —C$_{1-8}$ alkyl, —C$_{1-6}$ alkylcarbonyl, —C$_{1-6}$ alkylsulfonyl, and —C$_{1-6}$ alkoxycarbonyl,
(12) $C_{1-10}$alkylcarbonyl;
(13) arylcarbonyl, wherein:
   arylcarbonyl is phenylcarbonyl;
(14) ether-substituted $C_{1-10}$alkyl, wherein:
   ether-substituted $C_{1-10}$alkyl is selected from 1-methoxy-ethyl, and 1-ethoxy-ethyl;
(15) carboxylic ester, wherein:
   carboxylic ester is selected from $C_{1-10}$ carboxylic esters;
(16) carboxamide, wherein:
   carboxamides are selected from N,N-diisopropyl carboxamide, N-t-butyl carboxamide, N-(hydroxyphenyl) carboxamide, N-phenylcarboxamide, N-(aminophenyl) carboxamide, N-(carbomethoxy)phenyl carboxamide, N-(methoxycarboxy) phenyl carboxamide, N-acetamidophenyl-N-acetyl-carboxamide, N-acetamidophenyl-carboxamide, N-pivalamidophenyl carboxamide, and N-isobutyramidophenyl carboxamide;
(17) carbamate, wherein:
   carbamate is selected from t-butylcarbamate and isopropylcarbamate;
(18) substituted and unsubstituted anilide derivatives, wherein:
   substituted or unsubstituted anilide derivatives are selected from N-substituted-phenyl-carboxamides wherein the phenyl may be substituted with 1 to 2 substituents selected from ethyl, methyl, and trifluoromethyl;
(19) urea, wherein:
   urea is t-butylcarbonylamino urea;
(20) $C_{1-10}$ alkylureido $C_{0-5}$ alkyl, wherein:
   $C_{1-10}$ alkylureido $C_{0-5}$ alkyl is selected from: N-t-butylureidomethyl, N-n-propylureidomethyl, N-n-octylureidomethyl, and N-isopropylureido;
(21) substituted or unsubstituted arylureido $C_{0-5}$ alkyl, wherein:
   substituted or unsubstituted arylureido $C_{0-5}$ alkyl is selected from: N-(ethylphenyl) ureidomethyl, N-phenylureidomethyl, N-(methoxyphenyl) ureido, and 2-(ethoxyphenyl)ureidomethyl;
(22) $C_{1-10}$alkanoyloxy $C_{1-2}$alkyl, wherein:
   $C_{1-10}$alkanoyloxy$C_{1-2}$alkyl is selected from acetyloxymethyl, trimethylacetyloxymethyl, and (2-ethylhexamoyloxy)methyl;

(23) $C_{1-10}$ alkylcarbonylamino, wherein:
   $C_{1-10}$ alkylcarbonylamino is t-butylcarbonylamino;
(24) alkanoylamidoalkyl, wherein:
   alkanoylamidoalkyl is selected from: trimethylacetamidomethyl, carbomethoxyoctanoylamidomethyl, (isobutylphenyl)propionamidomethyl, 8-carboxyoctanoylamidomethyl, hydroxydodecanoyl amidomethyl, isopropyltioacetamidomethyl, benzyloxyacetamidomethyl, carbomethoxyacetamidomethyl, triphenylprropionamidomethyl, cyclohexylacetamidomethyl, methylcyclohexanecarboxamidomethyl, (3-hydroxy-4,4,4-trichlorobutyramido)methyl, and phenylthioacetamidomethyl;
(25) ether, wherein:
   ether is selected from ethylene ketal, and $C_{1-8}$ alkyl ether optionally substituted with hydroxy, halo, $C_{1-8}$ alkoxy, or aryl,
(26) thioether, wherein:
   thioether is selected from: $C_{1-8}$ alkylthio, phenylthio, and $C_{1-8}$ alkylthio substituted with phenyl; and
(27) substituted and unsubstituted aryl ether, wherein:
   substituted and unsubstituted aryl ether is selected from thiophenoxy, biphenyloxy, acetamidophenoxy, methylphenyloxy, phenyloxy, hydroxyphenyloxy, and methylsulfonylphenyloxy;

provided that when Z is

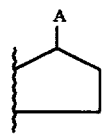

and

R is selected from H and $C_{1-5}$ alkyl, A is not $C_{1-10}$ alkyl; comprising:
dissolving the Δ-5 steroidal enelactam in a solvent in the presence of a rhodium based catalyst and treating with H$_2$ to preferentially yield a 5α-azasteroid.

2. The process of claim 1 wherein
(1) $C_{1-10}$ alkyl is selected from methyl, ethyl, propyl, butyl, pentyl, 1,5-dimethylhexyl, 6-methylhept-2-yl, and 1-methyl-4-isopropylhexyl;
(2) $C_{1-10}$ alkylcarbonyl is isobutylcarbonyl;
(3) carboxylic esters are $C_{1-10}$ alkylcarboxylic esters selected from carbomethoxy and carboethoxy.

3. The process of claim 1 wherein the rhodium based catalyst is Rh/C (5%) and the solvent is a $C_{1-6}$ alcohol.

4. The process of claim 3 wherein the solvent is ethanol.

5. The process of claim 1 wherein the rhodium based catalyst is Rh/Al$_2$O$_3$ (5%) and the solvent is a $C_{1-4}$ alkanoic acid.

6. The process of claim 5 wherein the solvent is acetic acid.

7. The process of claim 1 wherein the quantity of catalyst is adjusted so that the amount of rhodium in the reaction mixture is between 5–100% of the weight of the steroidal enelactam starting material.

8. The process of claim 7 wherein the quantity of catalyst is adjusted so that the amount of rhodium in the reaction mixture is between 10–20% of the weight of the steroidal enelactam starting material.

9. The process of claim 8 wherein the amount of catalyst is adjusted so that the amount of rhodium in the reaction mixture is about 20% of the weight of the steroidal enelactam starting material.

10. The process of claim 1 where the reaction is run at a H₂ pressure between 40–250 psi.

11. The process of claim 10 where the H₂ pressure is about 40 psi.

12. The process of claim 1 where the reaction is run at a temperature of 20°–30° C.

13. The process of claim 12 where the reaction is run at room temperature.

14. The process for the stereoselective reduction of claim 1 wherein Z is:

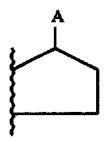

and A is selected from carboxyl or hydroxyl.

15. The process for the stereoselective reduction of claim 14 wherein R is selected from H and methyl and R¹ is methyl.